United States Patent [19]
Kramer et al.

[11] Patent Number: 4,518,798
[45] Date of Patent: May 21, 1985

[54] PREPARING ESTERS AND CARBOXYLIC ACIDS FROM LOWER OLEFINS

[75] Inventors: George M. Kramer; Walter Weissman, both of Berkeley Heights, N.J.; Herbert C. Brown, West Lafayette, Ind.; Rowland Pettit, deceased, late of Austin, Tex., by Flora H. Pettit, executrix

[73] Assignee: Exxon Research and Engineering Co., Florham Park, N.J.

[21] Appl. No.: 428,930

[22] Filed: Sep. 30, 1982

[51] Int. Cl.$^3$ .................. C07C 51/14; C07C 51/145; C07C 67/347
[52] U.S. Cl. ..................................... 560/233; 562/521
[58] Field of Search ......................... 560/233; 562/521

[56] References Cited

U.S. PATENT DOCUMENTS

| Re. 31,010 | 8/1982 | Gelbein | 560/233 |
| 2,768,968 | 10/1956 | Reppe et al. | 560/233 |
| 3,920,736 | 11/1975 | Gaenzler et al. | 562/521 |
| 4,256,913 | 3/1981 | Jung et al. | 560/233 |

Primary Examiner—Natalie Trousof
Assistant Examiner—Patricia M. Scott
Attorney, Agent, or Firm—Janet E. Hasak; Edward H. Mazer

[57] ABSTRACT

Esters or carboxylic acids are prepared from olefins containing at least two carbon atoms by reacting the olefin with carbon monoxide in the presence of:
 (i) a first complex of a selected Lewis acid with the ester or carboxylic acid, whichever is the reaction product recovered;
 (ii) a second complex of the Lewis acid with an alcohol, if an ester is being prepared, or with water, if a carboxylic acid is being prepared; and
 (iii) a metal carbonyl compound containing a Group IB transition metal in the first oxidation state; and by recovering the reaction product(s).

The preferred olefin is propylene, the preferred ester to be prepared is methylisobutyrate, the preferred metal is copper and the preferred Lewis acid is boron trifluoride.

17 Claims, No Drawings

PREPARING ESTERS AND CARBOXYLIC ACIDS FROM LOWER OLEFINS

BACKGROUND OF THE INVENTION

1. Field of the Invention

The present invention relates to a process for preparing esters and carboxylic acids from $C_2$ or higher olefins, preferably propylene, utilizing relatively mild reaction conditions and facile recovery procedures, and, in a further aspect, to a continuous process for such preparation.

2. Description of Related Patents

The conversion of propylene to its corresponding carboxylic acid or esters is an important process for the chemical manufacturing industry. For example, it has long been desired to find a convenient method for preparing high octane motor fuels and we have discovered that esters such as methylisobutyrate, which may be prepared from propylene, can be employed as a minor or major component of such motor fuels. In addition, methylisobutyrate may be employed as a solvent or as an intermediate in the synthesis of methylmethacrylate.

The Koch reaction, normally used to prepare carboxylic acids, provides a known path for the manufacture of esters or carboxylic acids when olefins are reacted with carbon monoxide and an alcohol or water in the presence of an acid such as sulfuric or phosphoric acid, hydrogen fluoride or boron trifluoride:water. The reaction sequence can be represented in general as follows:

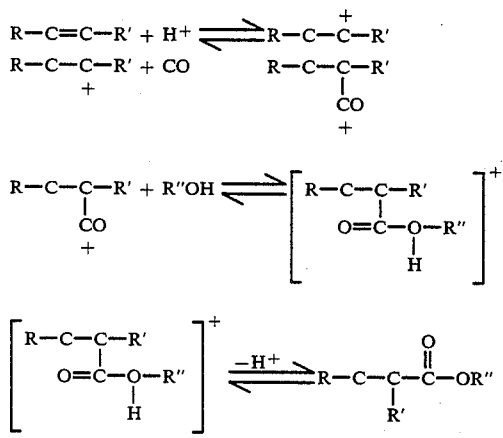

Generally, the Koch reaction is promoted when the acid is used in considerable excess over the amount of olefin or alcohol (or water) and the temperature is kept relatively low. A major disadvantage of this preparative route, however, is that the conversion of ethylene and propylene, which are less reactive olefins than branched olefins, to their respective ester or acid forms requires temperatures of 100° to 150° C. and pressures of 200–1000 atm, as disclosed in U.S. Pat. No. 2,378,009 and in J. R. Roland, et al., J.A.C.S., 72, 2122 (1950).

It is known from S. Pawlenko, Chem. Ing.-Techn., 40, 52 (1968) that oxonium tetrafluoroborates of the type $(ROH_2)^+ (BF_4)^-$ are catalysts for the batch esterification of olefins such as ethylene and propylene, which are ordinarily difficult to carboxylate, at 40°–50° C. and 100–150 atm total pressure.

U.S. Pat. No. 4,262,138 discloses the production of methylisobutyrate from propylene using an equimolar mixture of $BF_3$ to methanol generally under a pressure of 10–300 atm. Because the product is not easily recoverable (the $BF_3$ complexes therewith), the patent describes an elaborate distillation procedure for separating the acid from the ester.

It was discovered by Y. Matsushima, et al., Chem. Letters, 433 (1973) that carbon monoxide is absorbed by cuprous ion in $BF_3$—water systems under atmospheric pressure. Based on this discovery it was reported by Y. Souma, Osaka Kogyo Gijutsu Shikensho Hokoku, 79, 33b, 1–76 (1977) that in the presence of copper I or silver I salt the Koch reaction may be conducted at atmospheric pressures to convert linear olefins higher than propylene or branched olefins such as isobutylene to their respective carboxylic acids and esters. The copper I or silver I salt effectively increases the carbon monoxide concentration in the acid solution and leads to facile trapping of cationic intermediates involved in the reaction.

SUMMARY OF THE INVENTION

It has now been discovered that olefins containing at least two carbon atoms may be readily converted to their corresponding carboxylic acid or ester(s) under relatively mild conditions by utilizing as the acid catalyst solvent a mixture of a complex of Lewis acid:ester or Lewis acid:carboxylic acid and a complex of Lewis acid:alcohol or Lewis acid:water. The product is readily separated from the reaction mixture by adding an appropriate solvent thereto to extract the product, thus eliminating the necessity for distillation and facilitating the recovery of the Lewis acid for reuse.

Specifically, the present invention provides a process for preparing esters or carboxylic acids from olefins containing at least two carbon atoms which comprises the steps of:

(A) reacting said olefin or a mixture of said olefins with carbon monoxide in the presence of:

(i) a first complex of a Lewis acid with the ester or carboxylic acid, whichever is obtained as the reaction product from step (B), wherein the Lewis acid is characterized as being capable of forming a 1:1 molar complex with water which complex has an acid strength measured by a Hammett Acidity function value, $H_o$, of at least $-8.0$, and wherein the molar ratio of Lewis acid to ester or carboxylic acid is from about 1:1 to 2:1;

(ii) a second complex of said Lewis acid with a primary or secondary alcohol, if an ester is being prepared, or with water, if a carboxylic acid is being prepared, wherein the molar ratio of Lewis acid to alcohol or water is from about 1:1 to 2:1 and wherein the molar ratio of said first complex to said second complex initially is about 1:1 to 20:1; and (iii) a metal carbonyl compound, wherein the metal is a Group IB transition metal in the first oxidation state and the molar ratio of the metal carbonyl compound to the Lewis acid present is from 1:10 to 1:100,000; and (B) recovering the reaction product or mixture of products.

Due to the presence of an excess of a complex of Lewis acid:ester or Lewis acid:carboxylic acid in addition to the complex of Lewis acid:alcohol or Lewis acid:water, ready separation of the product from the Lewis acid is achieved at completion of the reaction. The preferred mode to aid in recovery of the product is to add to the reaction mixture a mixture of the alcohol or water and an inert extractant with respect to the reactants, products and catalyst or paraffinic liquid extractant. This ready separation results in regeneration of the Lewis acid for use in a continuous as well as a batch mode of operation.

In a preferred aspect of the invention the metal carbonyl compound is a salt containing a copper-I or silver-I carbonyl complex cation, the olefin is propylene which is reacted with a primary alcohol, and the Lewis acid is $BF_3$.

Most preferably, the present invention is directed to a process for preparing methylisobutyrate which comprises:

(A) reacting propylene with carbon monoxide at about 50°–70° C. and at a partial pressure of carbon monoxide of about 4 to 6 atmospheres in the presence of
  (i) a copper carbonyl compound, wherein copper is in the first oxidation state,
  (ii) $BF_3$:methylisobutyrate complex in an approximately 1:1 molar ratio, and
  (iii) $BF_3$:methanol complex in an approximately 1:1 molar ratio, wherein the molar ratio of the $BF_3$:methylisobutyrate complex to $BF_3$:methanol complex is from about 2.5:1 to 3.5:1 and the molar ratio of the copper carbonyl compound to $BF_3$ is from 1:200 to 1:300 and (B) recovering the methylisobutyrate as it is formed by displacement with a solution of methanol in an inert extractant.

It is noted that methylisobutyrate is the preferred product herein as it has a number of important uses, e.g., as a high octane blending component in motor fuels, as a component of fragrances, and as an intermediate in manufacturing methylmethacrylate.

DESCRIPTION OF THE PREFERRED EMBODIMENTS

The olefin employed in the process of this invention contains at least two carbon atoms, preferably $C_2$-$C_{20}$ olefins, and more preferably $C_2$-$C_6$ olefins. The olefins herein may be terminally or internally unsaturated linear or branched olefins or may be mixtures thereof, such as the isomers of butylene (n-butylene and isobutylene). Preferably the olefins are terminally unsaturated linear olefins, more preferably ethylene or propylene, and most preferably propylene.

In the process herein described the olefin, e.g., propylene, is reacted with carbon monoxide and with water, if a carboxylic acid, e.g., isobutyric acid, is to be prepared, or with a primary or secondary alcohol, if an ester is desired. For purposes herein a primary alcohol is preferred, and more particularly a lower (e.g., $C_1$-$C_{10}$) primary alcohol such as methanol, ethanol, propanol and butanol. Mixtures of alcohols may also be employed, but a mixture of products will result. The most preferred alcohol herein is methanol, which will produce methylisobutyrate.

For convenience, hereinafter throughout the specification, wherever the term "alcohol" is used, the word "water" can be substituted, unless otherwise specified. Similarly, wherever the word "ester" appears, the term "carboxylic acid" (which is the reaction product obtained when water is used as the reagent rather than alcohol) may be substituted therefor, unless otherwise noted. When propylene is the olefin being carbonylated, the carboxylic acid is isobutyric acid.

The metal carbonyl compound which must be present in the reaction mixture acts as a carbon monoxide carrier, thereby allowing the process to be carried out under milder conditions. The metal is a Group IB transition metal of the Periodic Table such as copper or silver and is present in the carbonyl compound in its first oxidation state. The carbonyl compound may be prepared in situ by adding to the acidic system provided by the Lewis acid complex and alcohol a salt of the metal in its first oxidation state. The metal in whatever its form reacts with the carbon monoxide present in the acidic reaction system to form the carbonyl compound. Thus, metal salts which are applicable herein for in situ preparation of the metal carbonyl include $Cu_2O$, $Ag_2O$, $Cu_2SO_4$, $Ag_2SO_4$, $AgClO_4$ and the like, with $Cu_2O$ and $Ag_2O$ being preferred. The practitioner will recognize that the reactivity of any of these salts with carbon monoxide will depend on the type of acid system, the concentration of alcohol, the acid strength of the Lewis acid, the temperature of the system (e.g., silver oxide may need to be added to cold $BF_3$ complex), the amount of metal added, the amount of complex and the molar ratio of Lewis acid to ester in the complex.

The amount of metal carbonyl compound in the reaction mixture will depend on many factors such as e.g., the type of metal and the reaction conditions, but generally the amount will be expressed as the mole ratio of metal carbonyl to Lewis acid present in the reaction mixture, which ranges from about 1:10 to 1:100,000, preferably 1:100 to 1:1000, and most preferably 1:200 to 1:300.

The complexes which must be present during the reaction herein are a Lewis acid:ester complex and a Lewis acid:alcohol complex. The Lewis acid is defined as having a coordination site available for accepting a pair of electrons donated by the Lewis base and as having an acid strength sufficient to ensure that an acidic complex with the alcohol will form. For purposes herein, the acid strength of the Lewis acid is defined in terms of the Hammett Acidity function $H_o$ of a 1:1 molar complex of the Lewis acid with water, as defined in M. J. Jorgenson and D. R. Hartter, J. Am. Chem. Soc., 85, 878 (1963). This function measures the ability of protonic acids (the Lewis acid:water complex) to protonate neutral molecules. The Lewis acid herein is defined as being capable of forming a 1:1 molar complex with water which complex has a Hammett Acidity function greater than $-8.0$, which is equivalent to the strength of about 82% $H_2SO_4$. Representative Lewis acids include boron trifluoride, aluminum trichloride, aluminum tribromide, boron trichloride, antimony pentafluoride, or mixtures thereof. Preferably $BF_3$ or $AlCl_3$ is employed, and most preferably $BF_3$. It is noted that the 1:1 molar complex of $BF_3$ to water has a Hammett Acidity function of about $-11$, as reported by C. H. Rochester, Acidity Functions (New York:Academic Press, 1970), p. 52.

The complexed ester applicable herein is the ester being produced in the reaction process. This ester should be comparably basic to or less basic than the alcohol from which it is formed so that addition of alcohol to a solution of the complexed ester will displace the ester thereby forming a Lewis acid:alcohol complex. During the reaction small amounts of side products, including higher molecular weight esters, may be produced but are not detrimental to the operation of the process and are displaced from their Lewis acid complexes on addition of alcohol.

The Lewis acid:ester and Lewis acid:alcohol complexes are prepared by adding to a mixture of the ester and alcohol a sufficient amount of the Lewis acid to form from about 1:1 to about 2:1 molar complexes, with the exact molar ratio dependent primarily on the Lewis acid and on the type of metal carbonyl compound, alcohol, and Lewis base employed, and on the reaction temperature. It is noted that with $BF_3$ the ratios of $BF_3$ to ester and of $BF_3$ to alcohol will generally be about 1:1, whereas with $AlCl_3$ and $SbF_5$ the ratios of $AlCl_3$ or $SbF_5$ to ester and of $AlCl_3$ or $SbF_5$ to alcohol are generally between about 1:1 and 2:1.

The relative amounts of the ingredients present in the reaction mixture are also important to the success of the process herein. Such a delicate balance of ingredients is necessary both to provide sufficient reactivity in a reasonable period of time and to allow for ready separation of the product from the reaction mixture. Thus, initially (before reaction) the mole ratio of the ester complex to the alcohol complex should range from about 1:1 to 20:1, preferably from 2:1 to 10:1, and most preferably from about 2.5:1 to 3.5:1, to provide the proton activity necessary to guarantee the presence of sufficient amounts of the metal carbonyl compound throughout the course of the reaction. Moreover, when uncomplexed alcohol is added with the olefin, at any one time there should never be an excess of alcohol over the amount of complexed ester present in the system, to avoid, in particular, later difficulties in recovery of the product. In addition, the molar ratio of added alcohol to olefin should preferably be no greater than about 1:1. The rate of addition of alcohol to the reaction mixture should thus be controlled to be about the same or less than the rate of addition of olefin thereto and controlled such that the molar ratio of ester to alcohol in the reactor is always greater than 1:1. In addition, the olefin addition rate should be maintained, in units of moles of olefin per hour to moles Lewis acid:alcohol complex, at between 1 to 20 and 5 to 1.

With respect to a specific catalyst system, the amounts of reagents are tabulated below:

| Catalyst System | Mole Ratio | Weight Ratio |
| --- | --- | --- |
| Methylisobutyrate Preparation: | | |
| Methylisobutyrate:methanol | 19:1 to 1:1 | 62.5:1 to 3.3:1 |
| $BF_3$:methylisobutyrate | 1:1 | |
| $BF_3$:methanol | 1:1 | |
| $AlCl_3$:methylisobutyrate | 1:1 to 2:1 | |
| $AlCl_3$:methanol | 1:1 to 2:1 | |
| $BF_3$:$Cu^I$ salt | | 10:1 to $10^5$:1 |
| $BF_3$:$Ag^I$ salt | | 10:1 to $10^5$:1 |
| Operating Conditions: | | |
| A. Batch | | within above ranges |
| B. Flow | | |
| Propylene:$BF_3$/methylisobutyrate (mole per hour:mole) | | 1:20 to 5:1 |
| Propylene:added methanol (mole:mole in reactor at all times) | >1:1 | |
| Methylisobutyrate:methanol (mole:mole in reactor at all times) | >1:1 | |

The reaction may be carried out in any apparatus which is suitable for conducting such a reaction, although equipment adapted for high pressure reactions need not be employed. One particularly convenient apparatus for the reaction herein is an autoclave; however, the process is not limited thereto. It is noted that equipment designed for a continuous mode of operation may be utilized if the complex is regenerated for reuse.

While the invention is not limited to any particular method of addition of ingredients, the sequence set forth below is ordinarily followed for best results. A mixture of alcohol, ester and metal salt is placed in the reactor and a Lewis acid is added in an amount to yield the molar ratios desired. The mixture is then saturated with carbon monoxide gas at between ambient and reaction temperature until the desired pressure is reached. Additional heat is thereafter applied to provide the desired reaction temperature, and olefin is added to the reaction mixture during stirring at a sufficiently slow rate to favor carbonylation over polymerization. If desired, additional alcohol may be added simultaneously with the olefin and, if so, is generally added at the same or a slower rate to avoid an excess thereof at any time. The reaction may be monitored by withdrawing samples of the mixture during stirring at predetermined time intervals and analyzing the samples for the amount of product(s) contained therein, as by nuclear magnetic resonance, gas chromatography, infrared spectrometry, mass spectrometry or any other suitable analytical techniques.

The reaction is generally conducted at temperatures of about 0°–90° C., preferably 20°–75° C., and most preferably 50°–70° C. Temperatures above about 90° C. are undesirable, as the metal carbonyl compound may lose its carbonyl groups or undergo redox reactions and the olefin may polymerize at excessive temperatures. The partial pressure of carbon monoxide for the reaction is ordinarily maintained at 1–100 atm, preferably 1–10 atm, and most preferably 4 to 6 atm.

The product or products may be recovered by adding an appropriate solvent to the reaction mixture and extracting. This separation allows for either continuous or batch processing. In the latter instance alcohol is allowed to react with the catalytic system. This results in the release of esters which are displaced into the extractant. The product is removed and additional olefin is added. After reaction of the olefin, additional alcohol is introduced and the cycle is repeated. In continuous operation the olefin and alcohol are added simultaneously with the extractant. The addition rates are adjusted so that the alcohol is added at or below the rate at which the olefin converts complexed alcohol to complexed ester. For many products a suitable extractant will consist of a non-polar solvent such as n-hexane.

In one typical continuous mode of operation for carrying out the process herein, a mixture of propylene, carbon monoxide, alcohol and hexane may be continuously fed into a $BF_3$:alcohol and $BF_3$:ester solution. The hexane serves as an extractant for the ester being displaced by incoming alcohol. The addition rates are adjusted so that the alcohol is added at or below the rate at which propylene converts complexed alcohol to complexed ester.

The invention is further illustrated by the following examples, which, however, are not to be taken as limiting in any respect. All parts and percentages, unless expressly stated to be otherwise, are by weight.

EXAMPLE 1

This example illustrates the preparation of the preferred product, methylisobutyrate, by the process of this invention.

A mixture of 0.312 mole of methanol and 0.975 mole of methylisobutyrate ester was blended with 0.01 mole of $Cu_2O$ in a 300 ml magnetically driven autoclave. A sample was withdrawn for analysis and the mixture was saturated with $BF_3$ gas at ambient temperature until the pressure in the system began to rise. This occurred after 1 mole of $BF_3$ per mole of alcohol and ester had been added. The excess $BF_3$ was vented off, the temperature raised to 50° C. and carbon monoxide added until a steady pressure of 4.9 atm (500 kPa) was obtained. The amount of CO absorbed by the system corresponded closely to that needed to prepare a $+^1Cu(CO)_4$ complex and saturate the vessel at 500 kPa.

The reactor was then heated to 63±3° C. and 0.056 mole of propylene was added from a charging bomb. A rapid increase and decrease in pressure followed the addition of propylene. After stirring for an hour a product sample was collected from the autoclave. The initial and product mixtures were analyzed by $^{13}C$ nuclear magnetic resonance. The data show that some of the methanol in the feed was converted to methylisobutyrate. Within experimental error the conversion corresponds to a quantitative reaction of the added propylene with methanol and carbon monoxide to form methylisobutyrate. The $^{13}CNMR$ spectra did not indicate the presence of products other than methylisobutyrate. The sensitivity of the analysis is such that no more than one percent of side products is believed to be present. The amounts of reactants and products, and the $^{13}C$-NMR results, are indicated in Table I. The C-NMR data were obtained by integration of the peaks produced by the methanol and ester.

TABLE I

| REACTANTS | MOLES | WT. % | BY $^{13}$C-NMR |
|---|---|---|---|
| Methanol | 0.312 | 11.2 | 11.7 ± 1.7 |
| Ester | 0.975 | 88.9 | 88.4 |
| $C_3H_6$ | 0.056 | | |
| $BF_3$ | 1.287 | | |
| $Cu_2O$ | 0.01 | | |
| PRODUCT, WT. % | | THEORY | BY $^{13}$C-NMR |
| Methanol | | 9.2 | 9.5 ± 1.3 |
| Ester | | 90.8 | 90.5 |

EXAMPLE 2

This example compares the operating conditions required to conduct the esterification of propylene using the instant system with those conditions required by two competitive processes for the carbonylation of linear olefins. The respective conditions are indicated in Table II.

TABLE II

| Parameters: | U.S. Pat. No. 2,378,009* | Chem. Ing-Techn., 40,* 52 (1968) | Present Invention |
|---|---|---|---|
| Olefin | Ethylene | Ethylene/ or Propylene | Propylene |
| Catalyst | $BF_3:H_2O$ + ROH | $HBF_4.H_2O$ (ROH) | $BF_3:CH_3OH$ + $BF_3$:methyl- isobutyrate + $+^1Cu(CO)_4$ |
| Temp. (°C.) | 100–150 | 40–50 | 63 ± 3 |
| Pressure (atm.) | 200–1000 | 100–150 | 5 |
| Product | Ester | Acid or Ester | Ester |
| Operation | | Batch | Batch or Flow |

*Comparative examples.

The last column shows that the instant process can be conducted at 5 atm., which is more than an order of magnitude less severe than the pressures used in alternative processes disclosed for linear olefins.

EXAMPLE 3

This example illustrates the preparation of isobutyric acid by the process of this invention.

A mixture of 0.050 mole of water, 0.450 mole of isobutyric acid, and 0.01 mole of $Cu_2O$ was analyzed by H-NMR spectroscopy to determine the ratio of protons on the methyl groups of the isobutyric acid to the sum of the water and acidic protons of the isobutyric acid. The mixture was then placed in a 300 ml autoclave as used in Example 1 and was saturated with $BF_3$ gas at ambient temperatures until the pressure in the system began to rise, i.e., after 1 mole of $BF_3$ per mole of alcohol and acid had been added. The excess $BF_3$ was vented off, the temperature raised to 60° C. and carbon monoxide added until a steady pressure of 3.9 atm (400 kPa) was obtained.

The reactor was then maintained at 60° C. and 0.076 mole of propylene was added from a charging bomb. After stirring for an hour a product sample was collected from the autoclave and analyzed by H-NMR for the same proton ratio as was measured for the reactant mixture. The spectra indicate that all of the water was converted to isobutyric acid. The amounts of reactants and products, and the H-NMR results, are shown in Table III.

TABLE III

| | | H-NMR ANALYSIS (Ratio of integrations of peaks of $CH_3$ to $H^+$) | |
|---|---|---|---|
| | | Theory | By H-NMR |
| REACTANTS | MOLES | | |
| $H_2O$ | 0.050 | 4.91 | 5.3 |
| Isobutyric Acid | 0.450 | | |
| $C_3H_6$ | 0.076 | | |
| $BF_3$ | 0.500 | | |
| CO | 5 | | |
| $Cu_2O$ | 0.01 | | |
| PRODUCTS | MOLE (if reaction is complete) | | |
| Isobutyric Acid | 0.526 | 6.0 | 5.9 |
| $H_2O$ | 0.0 | | |

In summary, the present invention is seen to provide an improved method for the carbonylation of olefins wherein the presence of a metal carbonyl compound and of a specified Lewis acid complexed with an alcohol (or water) and complexed with the carbonylated reaction product enables use of relatively mild reaction conditions and relatively simple recovery techniques.

While the invention has been described in connection with specific embodiments thereof, it will be understood that it is capable of further modification, and this application is intended to cover any variations, uses, or adaptations of the invention, following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process for preparing esters or carboxylic acids from an olefin feed comprising between two and four carbon atoms and added alcohol, if esters are being prepared, or water, if carboxylic acids are being prepared, which process comprises the steps of:

(A) reacting said olefin feed with carbon monoxide in the presence of:
  (i) a first complex of a Lewis acid with the ester or carboxylic acid, whichever is obtained as the reaction product from step (B), wherein the Lewis acid is characterized as being capable of forming a 1:1 molar complex with water which complex has an acid strength measured by a Hammett Acidity function value, $H_o$, of at least $-8.0$, and wherein the molar ratio of Lewis acid to ester or carboxylic acid is from about 1:1 to 2:1;
  (ii) a second complex of said Lewis acid with a primary or secondary alcohol, if an ester is being prepared, or with water, if a carboxylic acid is being prepared, wherein the molar ratio of Lewis acid to alcohol or water is from about 1:1 to 2:1, wherein the molar ratio of said first complex to said second complex initially is about 1:1 to 20:1 and wherein the molar ratio of said ester or carboxylic acid to said alcohol or water, respectively, is at all times greater than 1:1; and
  (iii) a metal carbonyl compound, wherein the metal is a Group IB transition metal in the first oxidation state and the molar ratio of the metal carbonyl compound to the Lewis acid present is from 1:10 to 1:100,000; and
(B) recovering the reaction product or mixture of products by displacement with a solution of a primary or secondary alcohol in an inert extractant if an ester is being produced or with water in an inert extractant if a carboxylic acid is being produced.

2. The process of claim 1 wherein said metal carbonyl compound is a salt containing a copper-I or silver-I carbonyl complex cation.

3. The process of claim 2 wherein sid metal carbonyl compound is prepared in situ from cuprous oxide or silver oxide.

4. The process of claim 1 wherein said Lewis acid is $BF_3$ or $AlCl_3$.

5. The process of claim 1 wherein said Lewis acid is $BF_3$ and the molar ratios in both the first and second complexes are 1:1.

6. The process of claim 1 wherein said olefin feed comprises ethylene and/or propylene.

7. The process of claim 1 wherein said olefin feed is propylene.

8. The process of claim 1 wherein said reaction is carried out at a temperature of about 0°–90° C. and at a partial pressure of carbon monoxide of 1 to 100 atm.

9. The process of claim 1 wherein said reaction is carried out at a temperature of 20°–75° C. and at a partial pressure of carbon monoxide of 1 to 10 atm.

10. The process of claim 1 wherein said first complex contains an ester and said second complex contains a primary alcohol.

11. The process of claim 1 wherein the molar ratio of said first complex to said second complex is about 2:1 to 10:1.

12. The process of claim 1 wherein the molar ratio of added alcohol or water to olefin is at all times no greater than 1:1.

13. The process of claim 1 or 12 wherein the reacting and recovering steps take place in a continuous mode.

14. The process of claim 1 wherein the molar ratio of the metal carbonyl compound to the Lewis acid present is from 1:100 to 1:1000.

15. A process for preparing methylisobutyrate comprising the steps of:
  (A) adding propylene and methanol to a reaction system;
  (B) reacting the propylene with carbon monoxide at about 50°–70° C. at a partial pressure of carbon monoxide of about 4 to 6 atmospheres in the presence of:
    (i) a first complex of $BF_3$ with methylisobutyrate having a molar ratio of $BF_3$ to methylisobutyrate of about 1:1;
    (ii) a second complex of $BF_3$ with methanol having a molar ratio of $BF_3$ to methanol of about 1:1, wherein the molar ratio of said first complex to said second complex is initially from about 2.5:1 to 3.5:1 and the molar ratio of added methanol to propylene is at all times no greater than 1:1 and such that the molar ratio of said methylisobutyrate to said methanol is at all times greater than 1:1; and
    (iii) a copper carbonyl compound wherein copper is in the first oxidation state and the molar ratio of copper carbonyl compound $BF_3$ is from 1:200 to 1:300; and
  (C) recovering the methylisobutyrate as it is formed by displacement with a solution of methanol in an inert extractant.

16. The process of claim 15 wherein said copper carbonyl compound is prepared in situ from cuprous oxide.

17. The process of claim 15 wherein the methylisobutyrate is recovered using n-hexane and the reacting and recovering steps take place in a continuous mode.

* * * * *